(12) United States Patent
Castens

(10) Patent No.: US 11,851,787 B2
(45) Date of Patent: Dec. 26, 2023

(54) WEAVING LOOM HAVING MOVABLE GUIDE BEAMS

(71) Applicant: Sybille Castens, Grossenkneten (DE)

(72) Inventor: Sybille Castens, Grossenkneten (DE)

( * ) Notice: Subject to any disclaimer, the term of this patent is extended or adjusted under 35 U.S.C. 154(b) by 155 days.

(21) Appl. No.: 17/601,093

(22) PCT Filed: May 11, 2021

(86) PCT No.: PCT/EP2021/062496
§ 371 (c)(1),
(2) Date: Oct. 4, 2021

(87) PCT Pub. No.: WO2021/228849
PCT Pub. Date: Nov. 18, 2021

(65) Prior Publication Data
US 2022/0298679 A1    Sep. 22, 2022

(30) Foreign Application Priority Data
May 12, 2020   (DE) .......................... 202020002061.3

(51) Int. Cl.
*D03C 13/00* (2006.01)
*D03D 41/00* (2006.01)
*D03C 9/06* (2006.01)

(52) U.S. Cl.
CPC .............. *D03C 13/00* (2013.01); *D03C 9/06* (2013.01); *D03D 41/002* (2013.01); *D03D 41/007* (2013.01)

(58) Field of Classification Search
CPC ........ D03C 13/00; D03C 9/06; D03D 41/002; D03D 41/007; A61P 31/04
See application file for complete search history.

(56) References Cited

U.S. PATENT DOCUMENTS

| | | | | |
|---|---|---|---|---|
| 427,105 A | * | 5/1890 | Morris | ................. D03D 41/002 139/195 |
| 738,479 A | * | 9/1903 | Pihl et al. | ................. D04G 1/08 87/53 |
| 868,228 A | * | 10/1907 | Thierry | ................. D03D 29/00 139/33 |
| 1,193,229 A | * | 8/1916 | Boyer | .................... D03D 39/02 139/4 |

(Continued)

FOREIGN PATENT DOCUMENTS

| | | |
|---|---|---|
| AT | 517089 A4 | 1/2021 |
| DE | 361359 C | 10/1922 |

(Continued)

OTHER PUBLICATIONS

WIPO, International Search Report (in a related application), dated Jul. 27, 2021.

(Continued)

*Primary Examiner* — Robert H Muromoto, Jr.
(74) *Attorney, Agent, or Firm* — Laurence P. Colton; SMITH TEMPEL BLAHA LLC

(57) ABSTRACT

A weaving loom for inserting continuous material, or loosely connected material or material in pieces, in which the warp threads run in the downward direction from the warp beam to the cloth beam and herein are individually held by hooks which are anchored in guide beams between the upper warp beams and the lower cloth beam.

22 Claims, 7 Drawing Sheets

(56) References Cited

U.S. PATENT DOCUMENTS

| | | | | | |
|---|---|---|---|---|---|
| 2,226,217 | A | * | 12/1940 | Brown | D03D 39/02 |
| | | | | | 139/7 A |
| 3,724,513 | A | * | 4/1973 | Pfarrwaller | D02H 13/28 |
| | | | | | 139/304 |
| 4,532,963 | A | * | 8/1985 | Bastion | D03C 3/20 |
| | | | | | 139/55.1 |
| 7,493,920 | B2 | * | 2/2009 | Vanderjeugt | D03C 3/44 |
| | | | | | 139/55.1 |
| 10,885,647 | B2 | * | 1/2021 | Tamarozzi | B60G 17/0185 |
| 11,167,503 | B2 | * | 11/2021 | Bonner | C08J 5/048 |
| 2002/0046778 | A1 | * | 4/2002 | Dewispelaere | D03C 3/24 |
| | | | | | 139/455 |
| 2016/0076174 | A1 | | 3/2016 | Sakaue | |

FOREIGN PATENT DOCUMENTS

| | | |
|---|---|---|
| DE | 1733292 U | 10/1956 |
| FR | 554820 A | 6/1923 |
| IT | FI20130079 A1 | 10/2014 |
| JP | 2005015954 A | 1/2005 |
| WO | 2007025765 A1 | 1/2021 |

OTHER PUBLICATIONS

Deutsches Patent- Und Markenamt (German Patent and Trademark Office), Recherchebericht (search in a related application), dated Jan. 15, 2021.

* cited by examiner

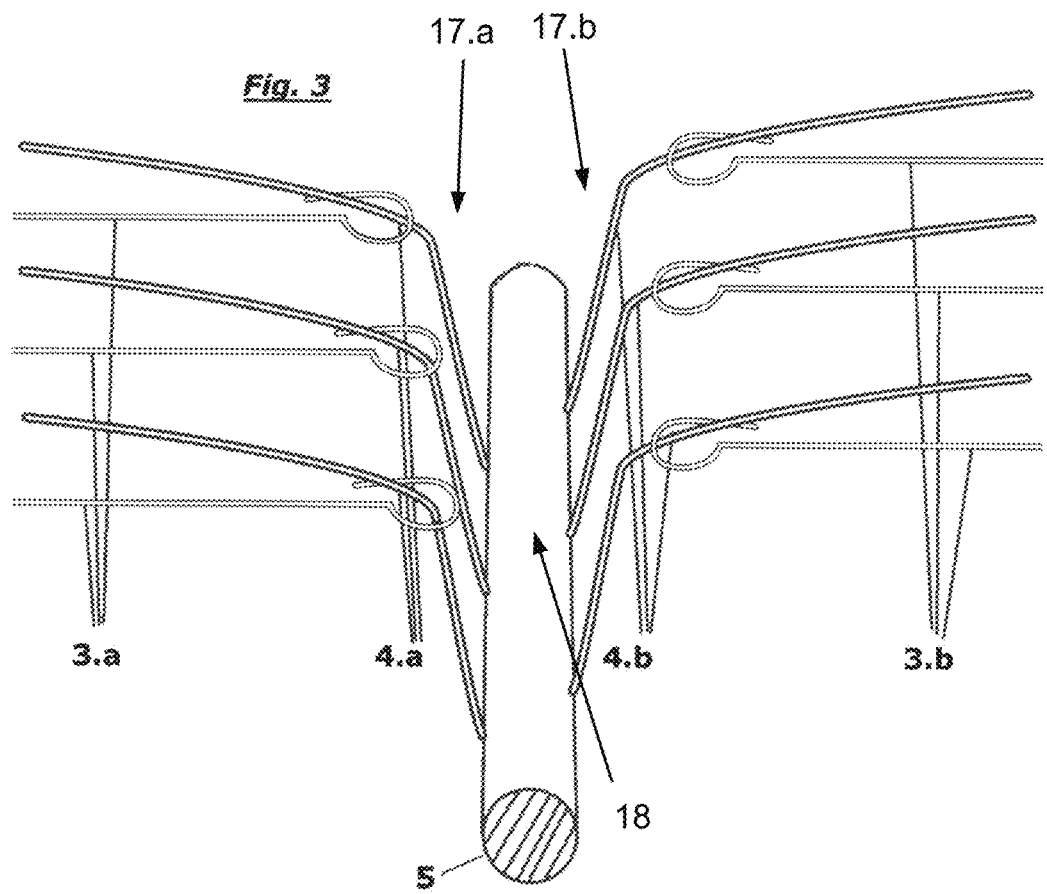
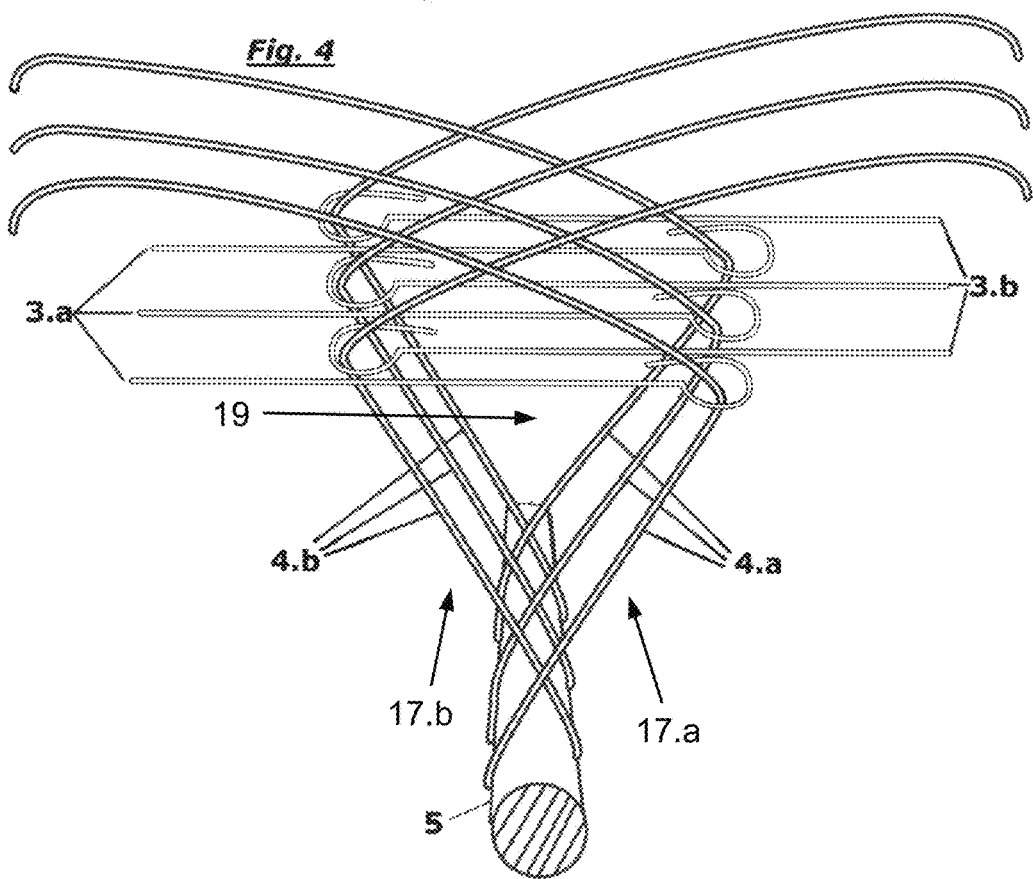

*Fig. 13*
*Fig. 12*
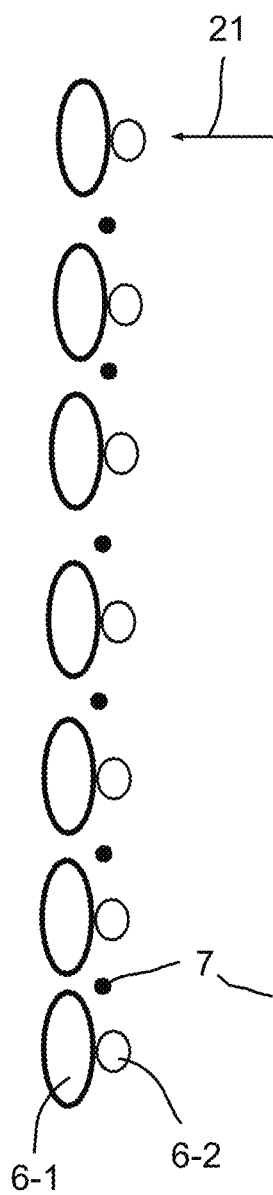
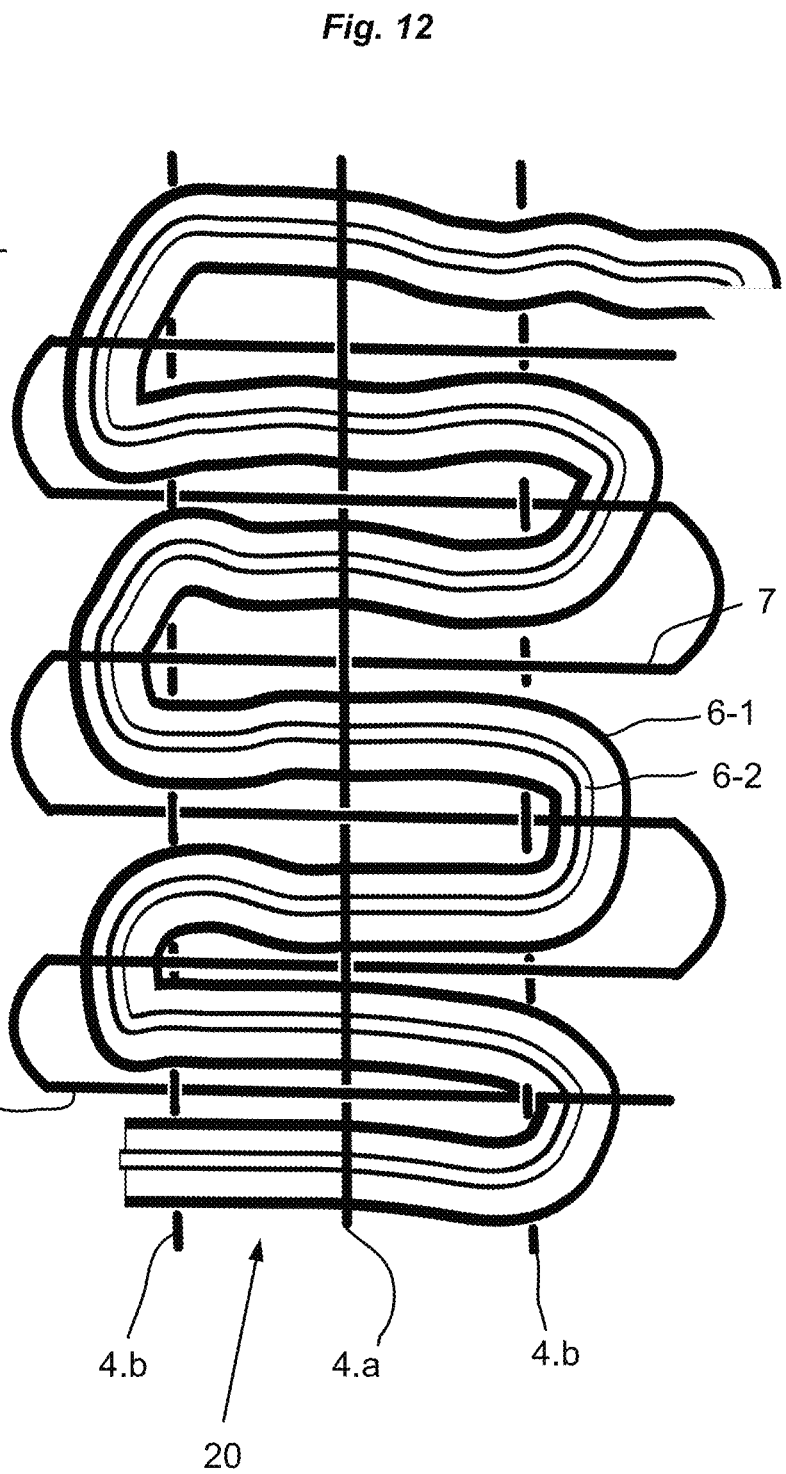

WEAVING LOOM HAVING MOVABLE GUIDE BEAMS

CROSS REFERENCE TO RELATED APPLICATIONS

This application is the United States national phase of, and claims priority on and the benefit of, International Application No. PCT/EP2021/062496 having an international filing date of 11 May 2021, which claims priority on and the benefit of German Patent Application No. 20 2020 002 061.3 having a filing date of 12 May 2020.

BACKGROUND OF THE INVENTION

Technical Field

The invention described here is based on the following issue. In flat weaving looms, a shed is delimited by four points and is thus enclosed toward the top: by warp threads held in the upper state; toward the bottom: by warp threads held in the lower state; toward the front: by previously woven fabric on the cloth beam; and toward the rear: by a reed.

Prior Art

As a result, it is indispensable for a weft thread to be transported through the respective shed from one side to the other side of the weaving loom. Serving to this end according to the current prior art are, shuttles on which a reserve of weft thread is wound; grippers which hand the weft thread through the shed, said weft thread being cut off after each insertion; nozzles which transport the weft thread by the force of air or water, said weft thread being cut off after each insertion.

The diameter of the weft thread is therefore delimited by the diameter of the shed, and the strength of said weft thread is also delimited by the respective technology used. The length of the weft thread is delimited by the storage capacity of the bobbing and the gripper, and in the case of nozzles delimited approximately by the width of the cloth.

It is thus not possible to convey a continuous material through the shed. Using the conventional technologies, loose material or loosely connected material cannot at all be moved to its place between the upper threads and the lower threads.

BRIEF SUMMARY OF THE INVENTION

This issue is solved by a weaving loom for inserting continuous material, or loosely connected material or material in pieces, characterized in that the warp threads run in the downward direction from the warp beam to the cloth beam and herein are individually held by hooks which are anchored in guide beams between the upper warp beams and the lower cloth beam, and as further disclosed herein.

This is achieved in that the weaving loom has been rotated by 90° in comparison to conventional flat weaving looms, such that the cloth beam is at the bottom. Furthermore, the rigid heddle system has been abandoned and, instead of disposing the heddles in shafts, each individual thread has been guided through a hook which is assigned to said thread and is anchored in rows in a guide beam. Even a loose material can now be placed from above the weaving loom, between these rows of hooks of the front guide beam and the rear guide beam and through said beams, onto the cloth beam, wherein the warp threads serve as a front delimitation and a rear delimitation, the choice of the loose material being delimited only by the mutual spacing of said warp threads. The cloth beam is situated below the respective formed shed and, by virtue of gravity, forms a natural detent toward the bottom.

Advantageously, the hooks on the two opposite guide beams lie opposite one another so as to be mutually offset, having an offset in the longitudinal direction of the guide beams.

Moreover, at least one of the two guide beams is to be movable so as to allow the hooks to mutually engage when the guide beams are converged, specifically so as to allow the hooks of the one guide beam to enter between the hooks of the other guide beam.

It is achieved by the invention that two different states in an alternating manner form two different sheds. In the open state (V-position), any material can be introduced which
 can be supported by the warp threads and the cloth beam;
 can be held in its position toward the front and the rear by the warp threads;
 in terms of the diameter does not exceed the length of the leg of the warp threads and the spacing from the cloth beam as a bisectrix in each insertion procedure.

The shed change takes place in that the front guide beam approaches the rear guide beam until a shed is formed by the now alternatingly crossed front and rear hooks, said shed being closed toward the top (crossed position). In the state closed toward the top, a thread is then introduced in the conventional manner, said thread in the open state stabilizing the introduced material toward the top.

The initial state is returned to as the next step, and the weaving recommences.

In this way, cables, hoses and other materials which must never be severed and which are longer than a shuttle can be stored on a bobbin of a shuttle can be woven. Loose material which to date has not been able to be stored on shuttles, or not been able to be handed over by means of grippers, or else has not been able to be propelled through the shed by an air jet or water jet can also be introduced.

Optionally, and according to the invention, the cloth beam and the guide beams can be disposed and aligned in such a manner that the warp threads of the one guide beam form a first warp thread plane, and the warp threads on the other guide beam form a second warp thread plane, and that the warp thread planes by way of a relative movement of the guide beams having the hooks are movable relative to one another. In particular, the warp thread planes extend from the guide beams up to the completed woven fabric above the cloth beam. The warp thread planes can also be curved or angled, in particular above the guide beams and in the direction toward the warp beams, by additionally provided guide members.

Optionally, and according to the invention, the warp thread planes in a relative position of the guide beams can form an open V-position, having a shed which is open toward the top, and having the cloth beam below the shed.

Optionally, and according to the invention, the warp thread planes by means of the guide beams can be movable from the open V-position to a crossed position and back again. The modification of the position of the warp thread plane causes the transition from the V-position through the crossed position and back again.

Optionally, and according to the invention, the warp thread planes at least in the crossed position can be angled or curved. The angulation is in particular defined by the guiding of the warp threads on the hooks. An angulation or curvature of the warp thread planes can however also be provided in the V-position, depending on the disposal of the warp beams and potential further guiding members for the warp threads.

Optionally, and according to the invention, the warp thread planes between the V-position and the crossed position can assume a flush, neutral position. The warp thread planes here become congruent.

Optionally, and according to the invention, at least two warp beams can be provided, each for receiving the warp threads of one of the warp thread planes, wherein the warp beams are disposed at a mutual spacing and the spacing preferably corresponds to at least a largest width of the V-shed. The location of the largest width is the highest location where the warp threads run obliquely downward to the guide beam, thus are not guided in a horizontal or upward manner.

Optionally, and according to the invention, two warp beams can be disposed at a mutual spacing, wherein each of the warp beams is assigned to one of the guide beams and holds the warp threads that are guided by the assigned guide beam. A first guide beam having a first warp beam lies opposite a second guide beam having a second warp beam.

Optionally, and according to the invention, the warp threads by way of the disposal of the warp beams and the disposal and mobility of the guide beams can be movable relative to one another between a V-position which is open at the top and a crossed position. In the crossed position, the warp threads of the one guide beam conjointly with the warp threads of the other guide beam form a closed shed for a weft thread which is to be introduced into the shed in a conventional manner.

Optionally, and according to the invention, the hooks in the crossed position can mutually mesh in such a manner that the hooks of the one guide beam are moved between the hooks of the other guide beam and past the hooks of the latter. In this way, the hooks of the one guide beam move up to a position close to the other guide beam.

Optionally and inventively, the guide beams can be subdivided into guide beam segments which are axially successive (in the longitudinal direction), wherein the guide beam segments are movable in a mutually independent manner. One hook or a plurality of hooks can be disposed on each guide beam segment. The guide beam segments are in particular movable between the V-position and the crossed position. Alternatively or additionally, the guide beam segments can be rotatable, preferably about a rotation axis parallel to the hook longitudinal direction. Rotatable guide beam segments are preferably provided with two or more hooks.

Optionally and inventively, the hooks can be configured so as to be open, closed, or closed but openable. Closed hooks correspond to rings. Open hooks have a gap for the entry of the warp threads, and openable hooks have a closable gap.

Optionally and inventively, the hooks can have an end-proximal hook curvature of at least 280 degrees, preferably of at least 370 degrees. The extent of the hook curvature here can also depend on the transition between the end-proximal hook curvature and the remaining part of the hook. An extent of the hook curvature in such a manner that the received warp thread remains within the hook curvature in the reciprocal movement of the hook is advantageous.

Optionally, and according to the invention, a first frame having a warp beam and a guide beam can be movable relative to a second frame having a warp beam and a guide beam, wherein preferably only one of the frames is movable.

The disposal of a warp beam and a guide beam in a common frame simplifies the construction of the weaving loom, as does the fixed disposal of the one frame while only the other frame is movable.

The subject matter of the invention also relates to a method for producing a woven fabric while using a weaving loom according to the invention.

Optionally, and according to the invention, in a crossed position of the weaving loom a weft thread can be introduced into the closed shed, wherein in a V-position of the weaving loom at least one material strand is placed into the then open shed. The material strand can be the continuation of the weft thread. However, the material thread is preferably different from the weft thread.

The subject matter of the invention also relates to a woven fabric having warp threads and weft threads, at least partially produced on a weaving loom according to the invention.

According to the invention, and optionally, material strands, or at least one continuous material strand, can be provided in the woven fabric parallel to the weft threads and alternating with the latter. The woven fabric, in an alternating manner with the weft threads, can also have a plurality of material strands and/or different material strands.

Optionally, and according to the invention, a wool strand, or a irrigation hose, or combinations thereof can be provided as material strands or as a material strand. The wool strand is in particular formed from one or a plurality of wool tops.

As a result of the production on the weaving loom according to the invention, the woven fabric can have entirely new and unexpected combinations of materials. An advantageous woven fabric as material strands has a combination of a wool top and an irrigation hose. The woven fabric can serve as a cover for soil to be irrigated. Plants can grow through the wool. The wool serves as a fertilizer or can additionally be provided with fertilizer material. Moreover, the wool prevents rapid evaporation of the water. Untreated wool acts in a hydrophobic manner such that the water is repelled by the wool.

Further features of the invention are derived from the remaining part of the description and from the claims.

BRIEF DESCRIPTION OF THE DRAWINGS

The technology will be explained in more detail by means of the illustrations of FIGS. 1-11, in which:

FIG. 3 and FIG. 4 show these lateral views additionally in a perspective manner;

FIG. 12 shows a woven fabric in the weaving loom; and

FIG. 13 shows a section through the threads or the material, respectively, in FIG. 12.

DETAILED DESCRIPTION OF PREFERRED EMBODIMENTS

Figure 1:
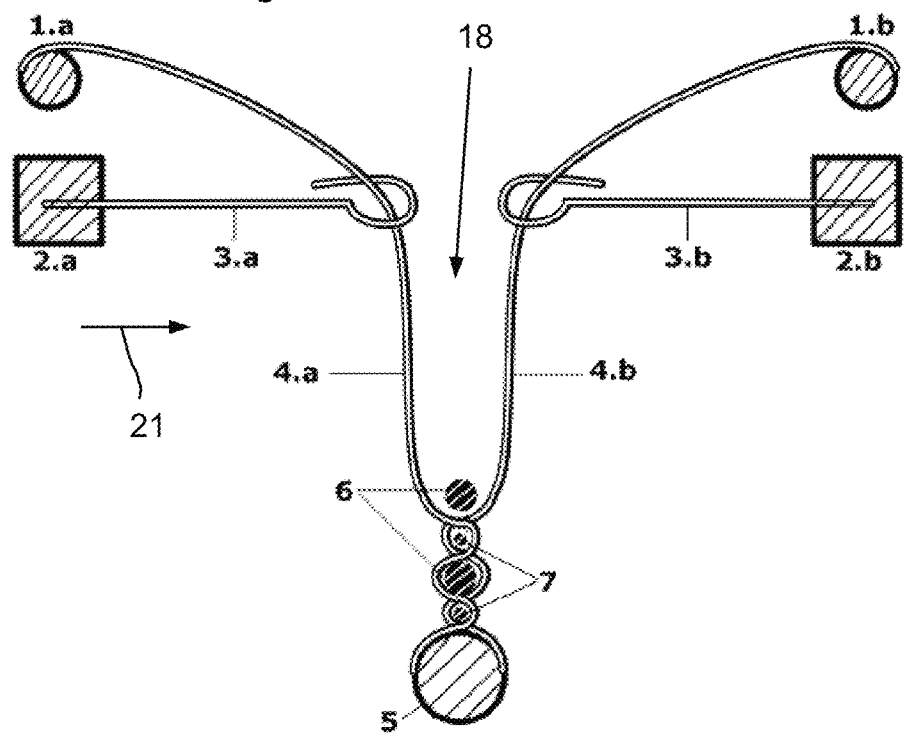
FIG. 1 and FIG. 2 show a simple lateral view.

For the sake of clarity, only those components that are relevant to the invention are illustrated. The number of hooks in FIG. 3 and FIG. 4 has been restricted to three hooks per guide beam in order for the principle of the technology to be explained.

The following applies to all illustrations: The front warp threads 4.$a$ run from the front warp beam 1.$a$ through the front hooks 3.$a$ anchored in the front guide beam 2.$a$ to the cloth beam 5. The rear warp threads 4.$a$ run from the rear warp beam 1.$b$ through the rear hooks 3.$b$ anchored in the rear guide beam 2.$b$ to the cloth beam 5.

The subdivision into a front guide beam and a rear guide beam is arbitrary and serves only for the purpose of differentiation and may also be reversed or be replaced by a right guide beam and a left guide beam, or by a first guide beam and a second guide beam. The same applies to other components present in pairs.

FIG. 1 and FIG. 3 illustrate the open shed state, specifically an open shed 18, during which the insertion of continuous material, loose material or loosely connected material 6 takes place between the non-crossed hooks 3.$a$ and 3.$b$.

Figure 2:
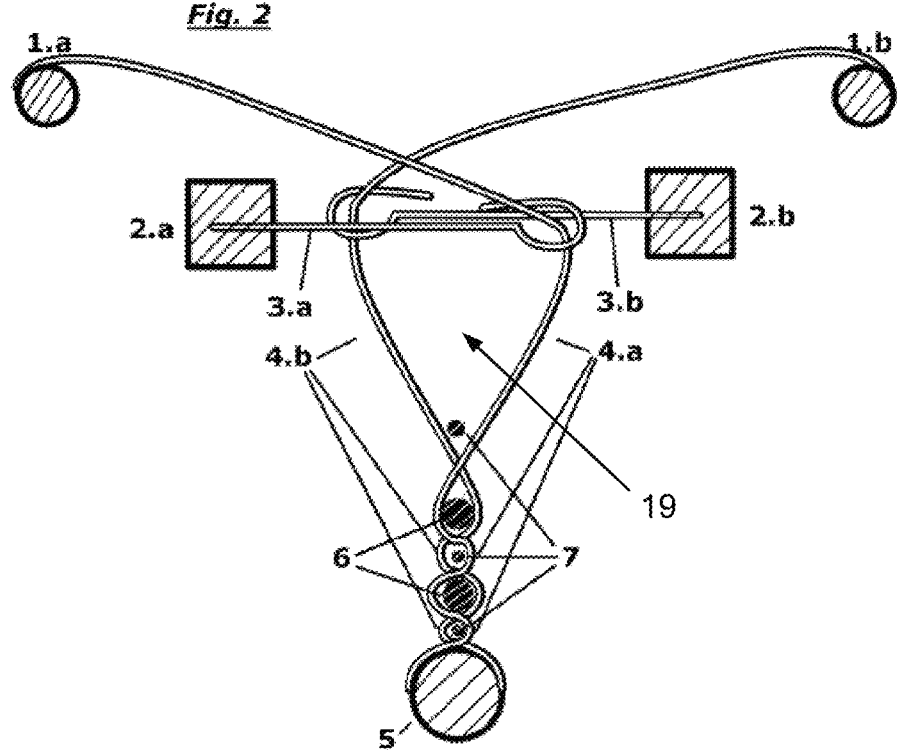

FIG. 2 and FIG. 4 show the closed state of the shed, specifically a closed shed 19, in which a conventional weft insertion 7 takes place while the hooks 3.$a$ and 3.$b$ are crossed.

As can be readily seen in FIGS. 3 and 4, the front warp threads 4.$a$ form a common warp thread plane 17.$a$, and the rear warp threads 4.$b$ form a rear warp thread plane 17.$b$. The warp thread planes 17.$a$, 17.$b$ in FIG. 3 form the open V-shed. The warp thread planes 17.$a$ and 17.$b$ in FIG. 4 are mutually crossed and, in conjunction with the deflection of the warp threads 4.$a$, 4.$b$ in the region of the hooks 3.$a$, 3.$b$, form a closed shed.

Figure 5:
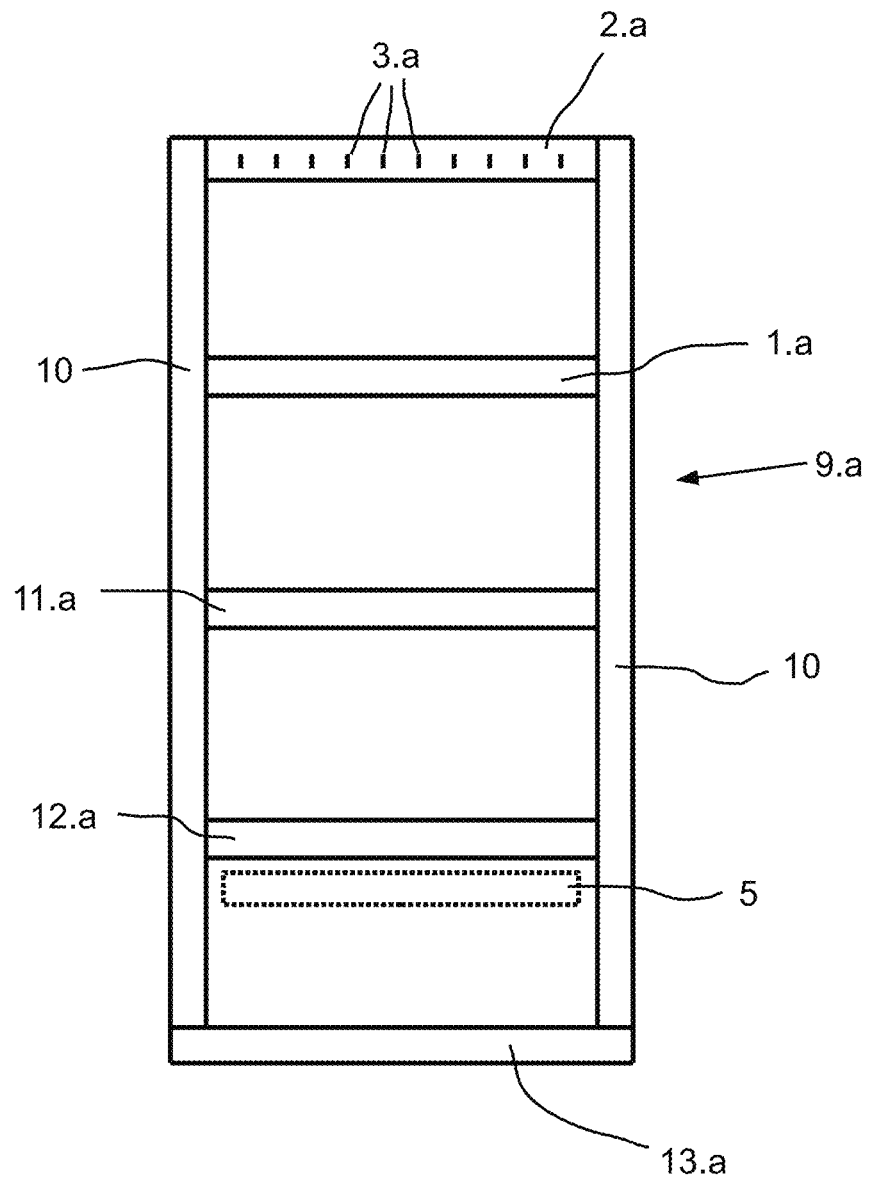
FIG. 5 shows a lateral elevation of a frame.
Figure 6:
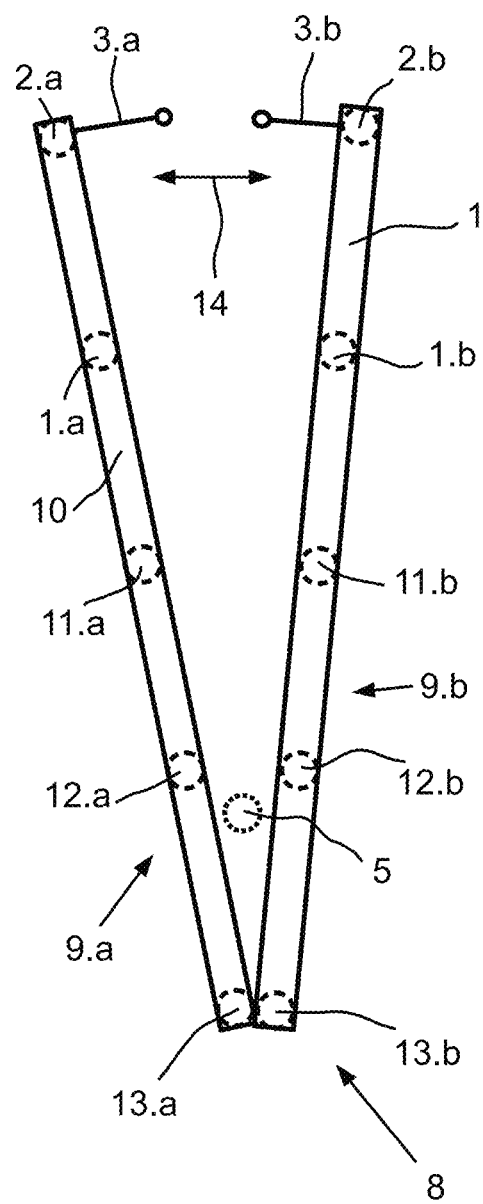
FIG. 6 shows a weaving loom having two frames in the V-position, in a lateral view.
Figure 7:
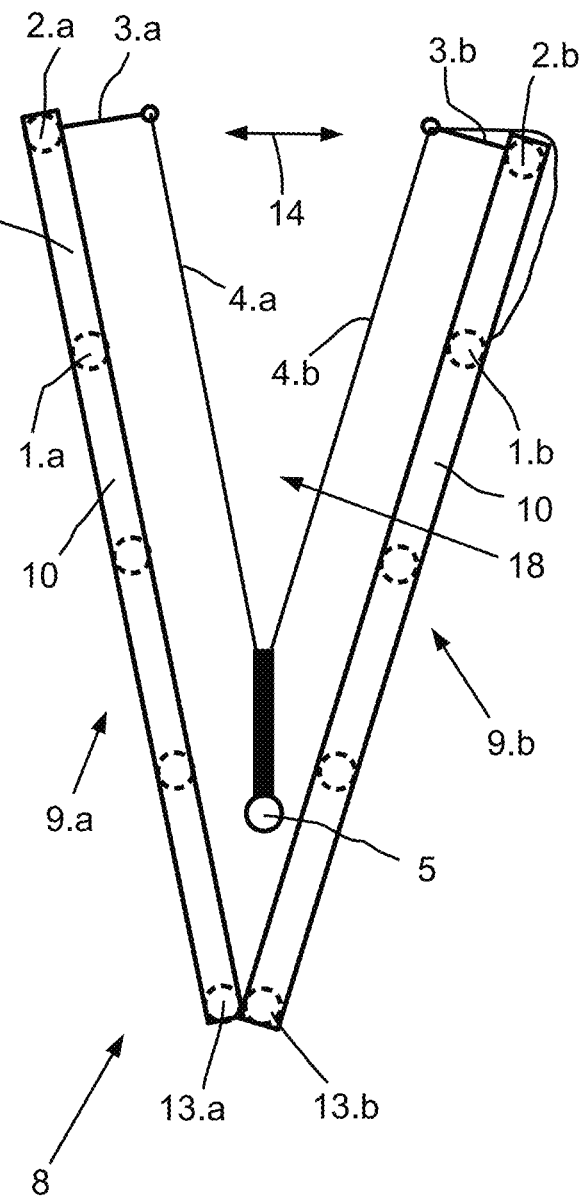
FIG. 7 shows the weaving loom according to FIG. 6 in a modified position.

A weaving loom 8 according to the invention can have substantially two frames 9.$a$, 9.$b$, as is illustrated in FIGS. 6 and 7. FIG. 5 shows the frame 9.$a$ in a front view. Component parts of the frame 9.$a$ that can be seen are: external upright longitudinal rails 10, the front guide beam 2.$a$ as an upper completion, below and spaced apart therefrom the front warp beam 1.$a$, below and spaced apart therefrom two support beams 11.$a$, 12.$a$, and as a lower completion an articulated beam 13.$a$.

The two frames 9.$a$, 9$b$ in the region of the articulated beams 13.$a$, 13.$b$ are connected to one another in an articulated manner not illustrated in more detail, such that the frames 9.$a$, 9.$b$ are pivotable toward one another and in the opposite direction, see double arrow 14.

One of the two frames 9.$a$, 9.$b$ is preferably mounted so as to be stationary, while the other frame is held so as to be pivotable. However, both frames 9.$a$, 9.$b$ can be disposed in a pivotable manner.

FIG. 7 shows the open V-position of the weaving loom 8, or of the warp threads 4.$a$, 4.$b$, respectively. The two frames 9.$a$, 9.$b$ in FIG. 6 are pivoted to a somewhat closer position than in FIG. 7. This is merely an intermediate position on the way to the crossed position which is derived from FIGS. 2 and 4.

The warp thread 4.$b$ in FIG. 7 above the hook 3.$b$ is guided about the guide beam 2.$b$ and downward to the warp beam 1.$b$ and held on the latter. This applies in an analogous manner to the warp thread 4.$a$ but is not explicitly plotted there.

In the illustration of FIG. 7, the warp thread 4.$b$ runs loosely from the guide beam 2.$b$ to the warp beam 1.$b$. This illustration has been chosen only so as to be able to clearly show the warp thread 4.$b$ at this location. In actual fact, the warp thread is preferably tensioned so as to be taut up to the warp beam 1.$b$.

The cloth beam 5 is indicated only by dashed lines in FIG. 6, and the warp threads 4.$a$, 4.$b$ are not plotted for reasons of improved clarity.

Figure 8:
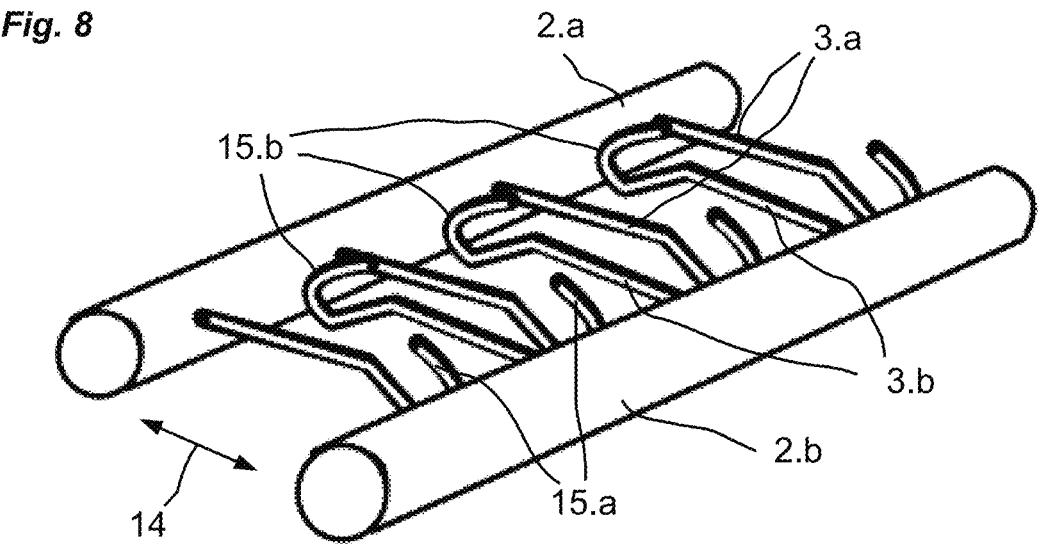
FIG. 8 shows guide beams having hooks in a crossed position.
Figure 9:
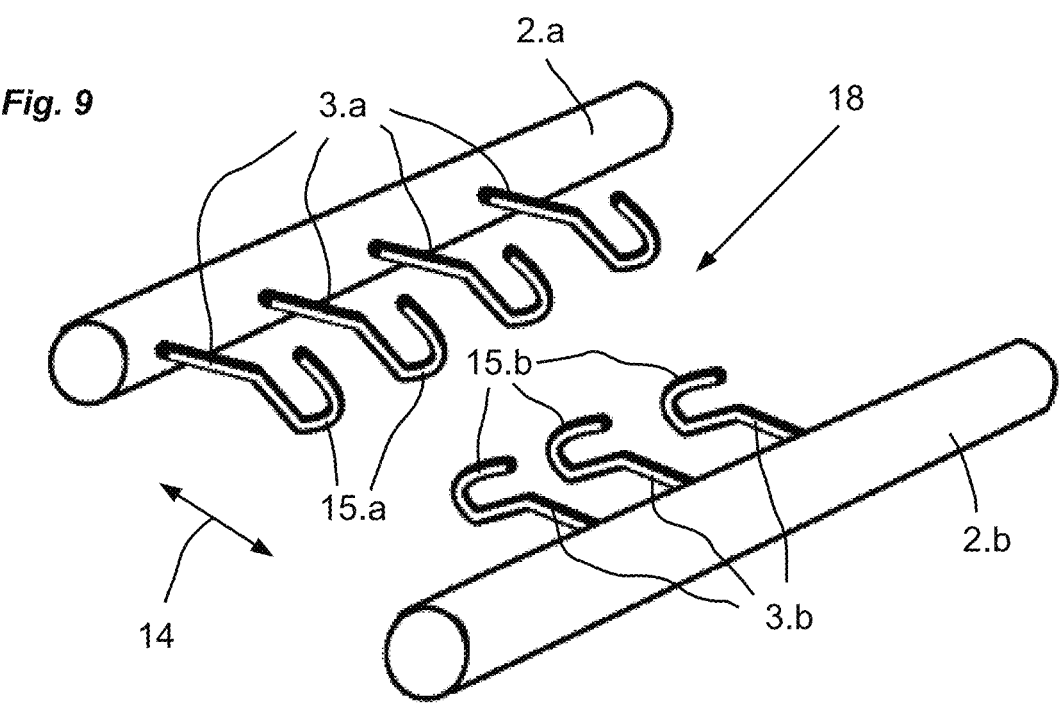
FIG. 9 shows guide beams having hooks in an open V-position.
Figure 10:
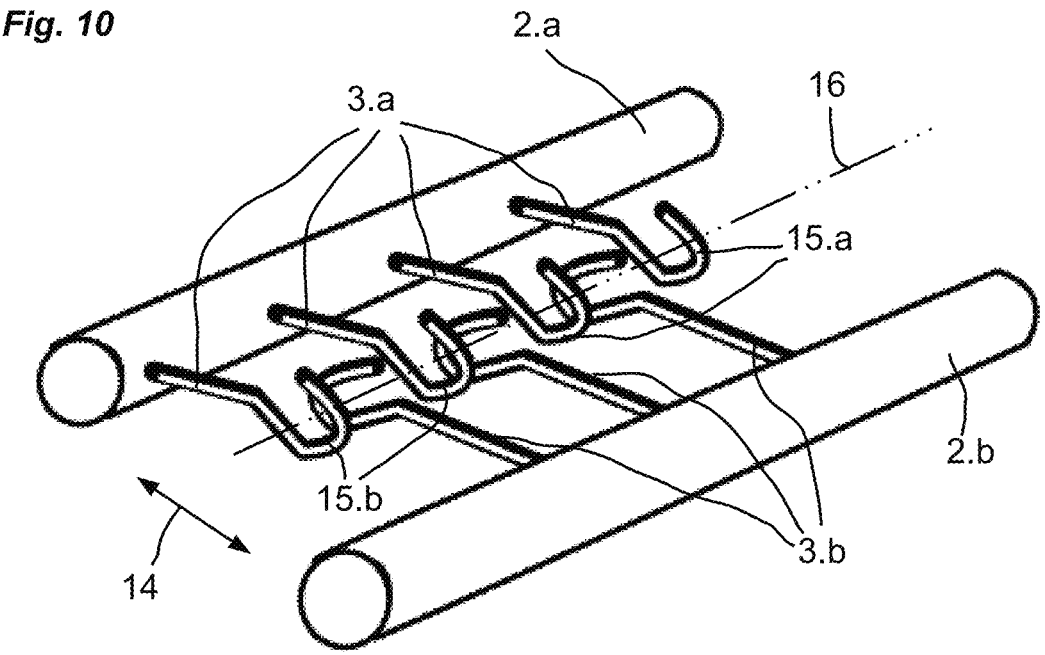
FIG. 10 shows guide beams having hooks in a neutral position.

FIGS. 8, 9, and 10 show the potential relative movement of the guide beams 2.$a$, 2.$b$ having the hooks 3.$a$, 3.$b$. FIG. 9 corresponds approximately to the illustration in FIG. 7, having the open V-position and guide beams 2.$a$, 2.$b$ which are widely diverged, also matching FIGS. 1 and 3. End-proximal curvatures 15 for receiving the warp threads 4.$a$, 4.$b$ of the hooks 3.$a$, 3.$b$ have a significant mutual spacing in the direction of the arrow 14. The hooks 3.$a$, 3.$b$ preferably lie approximately in a common horizontal plane.

FIG. 8 shows the crossed position, analogous to that in FIGS. 2 and 4. The guide beams 2.$a$, 2.$b$ are converged to the extent that this is possible counter to the extent of the hooks 3.$a$, 3.$b$. The hooks 3.$a$ of the guide beam 2.$a$ mesh with the hooks 3.$b$ of the guide beam 2.$b$ such that the end-proximal curvatures 15.$a$ of the hooks 3.$a$ in the direction toward the opposite guide beam 2.$b$, or 2.$a$, respectively, are moved past the end-proximal curvatures 15.$b$ of the hooks 3.$b$.

FIG. 10 shows an intermediate position of the guide beams 2.$a$, 2.$b$ in which the end-proximal curvatures 15.$a$, 15.$b$ of both guide beams 2.$a$, 2.$b$ are aligned along a common line 16. The intermediate position can also be referred to as a neutral position or I-position. In the practical application of the weaving loom, the intermediate position is normally past through without stoppage.

Figure 11:
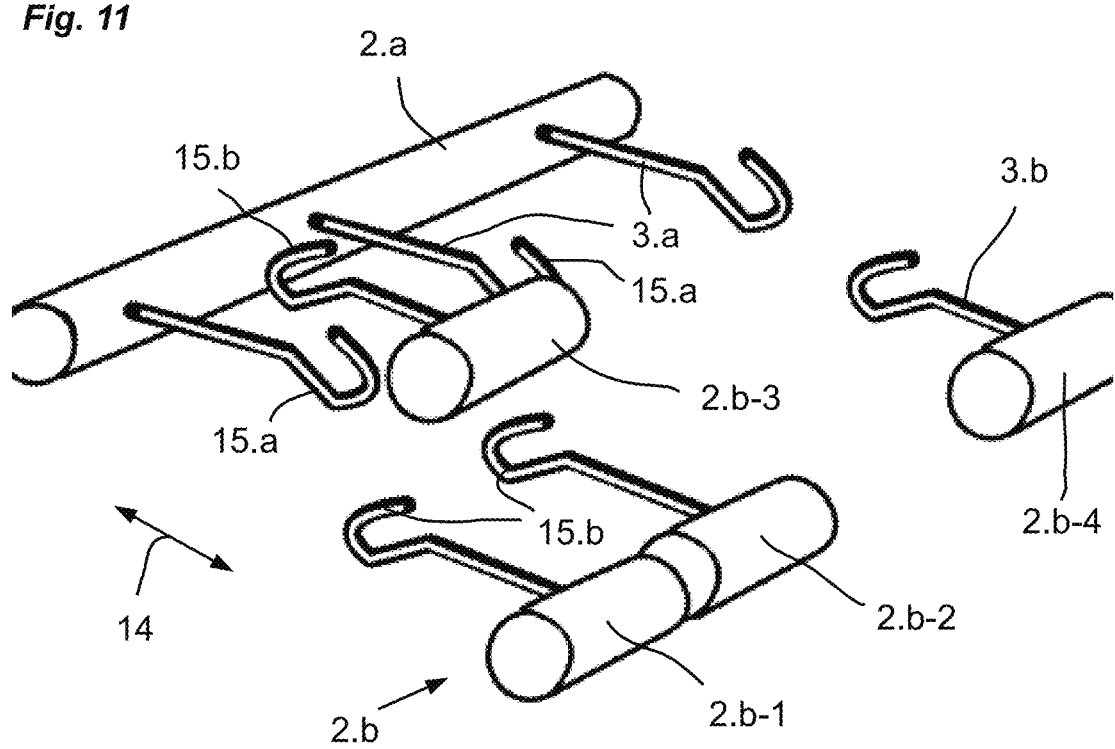
FIG. 11 shows an integral guide beam and a segmented guide beam.

FIG. 11 shows a particularity in the design of the guide beam 2.$b$. The latter in the longitudinal direction is subdivided into individual guide beam segments 2.$b$-1, 2.$b$-2, 2.$b$-3, 2.$b$-4, etc. Each guide beam segment is movable in the direction of the arrow 14 independently of the other guide beam segments. Mountings and drives suitable to this end are not plotted. The guide beam segment 2.$b$-3 in an exemplary manner is shown in the crossed position according to FIG. 8, while the remaining guide beam segments assume the open V-position according to FIG. 9. As a result of the described segmentation of the guide beam 2.$b$ it is possible for special weaving patterns to be generated.

As a result of the independent mobility of the guide beam segments, the uniformity of the warp thread plane 17.$b$ can be abolished. In the position according to FIG. 11, a warp thread on the guide beam segment 2.$b$-3 would no longer be a component part of the warp thread plane 17.$b$.

Each guide beam segment 2.$b$-1 to 2.$b$-4 in FIG. 11 has in each case one hook 3.$b$. Another allocation is also possible, for instance having two or more hooks per guide beam segment.

Rotating adjacent warp threads is possible, for example by way of rotatable guide beam segments having in each case two hooks 3.$b$. The rotation preferably takes place about a rotation axis parallel to the arrow 14.

Only the guide beam 2.$b$ having guide beam segments is illustrated in FIG. 11. Alternatively or additionally, the other guide beam 2.$a$ can also be configured in segments.

The end-proximal curvatures 15.$a$, 15.$b$ of the hooks 3.$a$, 3.$b$ are illustrated in a simplified manner in the figures. In actual fact, the curvatures 15.$a$, 15.$b$ are configured in such a manner that the warp threads 4.a, 4.b by said curvatures 15.a, 15.b can be actively moved in both directions of the arrow 14. In order for this to be achieved, the end-proximal curvatures 15.a, 15.b can also be configured as a closed ring, or as an open ring, such that the warp threads 4.a, 4.b can be placed into the curvatures 15.a, 15.b by a lateral movement. The end-proximal curvatures 15.a, 15.b should extend at least across an angle of more than 270 degrees, preferably more than 360 degrees, depending on the design of the transition between the end-proximal curvatures and the remaining part of the hook 3.a, 3.b.

Products of a very individual type can be produced using the weaving loom 8 according to the invention. Materials which are not weft-capable can be placed into the open shed 18 of the V-position according to FIGS. 1, 3, 7, and 9. Materials which are not weft-capable are, for example, particularly thick, bulky, stiff materials and/or continuous materials. Other combinations of these materials are also possible. For example, a soil cover having an irrigation function can be produced in that a wool strand 6-1 conjointly with the continuous irrigation hose 6-2 is in each case placed into the open V-position.

FIG. 12 shows a woven fabric 20 formed in this manner during weaving, in a viewing direction according to the arrow 21 in FIGS. 1 and 13. The threads 7 and materials 6-1, 6-2 placed in the weft direction are shown in a sectional view in FIG. 13, in a manner corresponding to that of FIG. 12. The weft threads 7, which may also be referred to as a stabilizing thread, alternates with the combination of the wool strand 6-1 and the irrigation hose 6-2. The irrigation hose 6-2 here lies next to, or in front of, respectively, the wool strand 6-1, but may also be enclosed by the wool strand or lie above/below the latter.

LIST OF REFERENCE SIGNS 1.a Front warp beam
1.b Rear warp beam
2.a Front guide beam
2.b Rear guide beam
2.b-1 Guide beam segment
2.b-2 Guide beam segment
2.b-3 Guide beam segment
2.b-4 Guide beam segment
3.a Front hook
3.b Rear hook
4.a Front warp thread
4.b Rear warp thread
5 Cloth beam
6 Continuous, loose material, or loosely connected material
6-1 Wool strand
6-2 Irrigation hose
7 Weft insertion using conventional technology
8 Weaving loom
9.a Frame
9.b Frame
10 Longitudinal rail
11.a Support beam
11.b Support beam
12.a Support beam
12.b Support beam
13.a Articulated beam
13.b Articulated beam
14 Arrow
15.a End-proximal curvatures
15.b End-proximal curvatures
16 Line
17.a Warp thread plane
17.b Warp thread plane
18 Open shed
19 Closed shed
20 Woven fabric
21 Arrow

The invention claimed is:

1. A weaving loom for inserting continuous material, or loosely connected material or material in pieces, the weaving loom comprising warp beams (1.a, 1.b), a cloth beam (5), hooks (3.a, 3.b), and guide beams (2.a, 2.b),
wherein warp threads (4.a and 4.b) run in a downward direction from the warp beams (1.a and 1.b) to the cloth beam (5) and herein are individually held by the hooks (3.a and 3.b) which are anchored in the guide beams (2.a and 2.b) between the warp beams (1.a and 1.b) and the cloth beam (5), the warp beams (1.a and 1.b) being located above the cloth beam (5),
wherein the cloth beam (5) and the guide beams (2.a, 2.b) are disposed and aligned in such a manner that the warp threads (4.a) of one the guide beams (2.a) form a first warp thread plane (17.a), and the warp threads (4.b) of the other of the guide beams (2.b) form a second warp thread plane (17.b), and that the warp thread planes (17.a, 17. b) by way of a relative movement of the guide beams (2.a, 2.b) having the hooks (3.a, 3.b) are movable relative to one another,
wherein the warp thread planes (17.a, 17.b) by means of the guide beams (2.a, 2.b) are movable from an open V-position to a crossed position and back again, and
wherein the warp thread planes (17.a, 17.b) between the V-position and the crossed position can assume a flush position.

2. The weaving loom as claimed in claim 1, wherein the hooks (3.a and 3.b) on two opposite of the guide beams (2.a and 2.b) lie opposite one another so as to be mutually offset.

3. The weaving loom as claimed in claim 2, wherein at least one of the guide beams (2.a, 2.b) is movable towards the other one of the guide beams (2.a, 2.b) so as to converge the guide beams (2.a, 2.b) to each other and so to allow the hooks (3.a and 3.b) to mutually engage when the guide beams (2.a and 2.b) are converged.

4. The weaving loom as claimed in claim 1, wherein the warp thread planes (17.a, 17.b) in a relative position form an open V-position, having a V-shed (18) which is open toward the top, and having the cloth beam (5) below the V-shed (18).

5. The weaving loom as claimed in claim 1, wherein the warp thread planes (17.a, 17.b) at least in the crossed position can be angled or curved.

6. The weaving loom as claimed in claim 4, wherein at least two of the warp beams (1.a, 1.b) are provided, each for receiving the warp threads (4.a, 4.b) of one of the warp thread planes (17.a, 17.b), wherein the warp beams (1.a, 1.b) are disposed at a mutual spacing.

7. The weaving loom as claimed in claim 1, the warp beams (1.a, 1.b) are disposed at a mutual spacing from each other, wherein each of the warp beams (1.a, 1.b) is assigned to one of the guide beams (2.a, 2.b) and holds the warp threads (4.a, 4.b) that are guided by the assigned one of the guide beams (2.a, 2.b).

8. A weaving loom for inserting continuous material, or loosely connected material or material in pieces, the weaving loom comprising warp beams (1.a, 1.b), a cloth beam (5), hooks (3.a, 3.b), and guide beams (2.a, 2.b), wherein warp threads (4.*a* and 4.*b*) run in a downward direction from the warp beams (1.*a* and 1.*b*) to the cloth beam (5) and herein are individually held in the hooks (3.*a* and 3.*b*) which are anchored in the guide beams (2.*a* and 2.*b*) between the warp beams (1.*a* and 1.*b*) and the cloth beam (5), the warp beams (1.*a* and 1.*b*) being located above the cloth beam (5), wherein at least one of the guide beams (2.*a*, 2.*b*) is movable to converge the guide beams (2.*a*, 2.*b*) to each other, and wherein the warp threads (4.*a*, 4.*b*) by way of the disposal of the warp beams (1.*a*, 1.*b*) and the disposal and mobility of the guide beams (2.*a*, 2.*b*) are movable relative to one another between a V-position which is open at the top and a crossed position.

9. The weaving loom as claimed in claim 8, wherein the hooks (3.*a*, 3.*b*) in the crossed position mutually mesh such that the hooks (3.*a*) of one of the guide beams (2.*a*) are moved between the hooks (3.*b*) of another of the guide beams (2.*b*) and past the hooks (3.*b*) of the another of the guide beams (2.*b*).

10. A weaving loom for inserting continuous material, or loosely connected material or material in pieces, the weaving loom comprising warp beams (1.*a*, 1.*b*), a cloth beam (5), hooks (3.*a*, 3.*b*), and guide beams (2.*a*, 2.*b*), wherein warp threads (4.*a* and 4.*b*) run in a downward direction from the warp beams (1.*a* and 1.*b*) to the cloth beam (5) and herein are individually held in the hooks (3.*a* and 3.*b*) which are anchored in the guide beams (2.*a* and 2.*b*) between the warp beams (1.*a* and 1.*b*) and the cloth beam (5), the warp beams (1.*a* and 1.*b*) being located above the cloth beam (5), and wherein the guide beams (2.*a*, 2.*b*) are subdivided into guide beams segments (2.*b*-1, 2.*b*-2, 2.*b*-3, 2.*b*-4) which are successive in the longitudinal direction, wherein the guide beam segments (2.*b*-1, 2.*b*-2, 2.*b*-3, 2.*b*-4) are movable in a mutually independent manner.

11. The weaving loom as claimed in claim 1, wherein the hooks (3.*a*, 3.*b*) are configured so as to be open, closed, or closed but openable.

12. A weaving loom for inserting continuous material, or loosely connected material or material in pieces, the weaving loom comprising warp beams (1.*a*, 1.*b*), a cloth beam (5), hooks (3.*a*, 3.*b*), and guide beams (2.*a*, 2.*b*), wherein warp threads (4.*a* and 4.*b*) run in a downward direction from the warp beams (1.*a* and 1.*b*) to the cloth beam (5) and herein are individually held in the hooks (3.*a* and 3.*b*) which are anchored in the guide beams (2.*a* and 2.*b*) between the warp beams (1.*a* and 1.*b*) and the cloth beam (5), the warp beams (1.*a* and 1.*b*) being located above the cloth beam (5), wherein the hooks (3.*a*, 3.*b*) have an end-proximal hook curvature of at least 280 degrees.

13. A weaving loom for inserting continuous material, or loosely connected material or material in pieces, the weaving loom comprising warp beams (1.*a*, 1.*b*), a cloth beam (5), hooks (3.*a*, 3.*b*), and guide beams (2.*a*, 2.*b*), wherein warp threads (4.*a* and 4.*b*) run in a downward direction from the warp beams (1.*a* and 1.*b*) to the cloth beam (5) and herein are individually held in the hooks (3.*a* and 3.*b*) which are anchored in the guide beams (2.*a* and 2.*b*) between the warp beams (1.*a* and 1.*b*) and the cloth beam (5), the warp beams (1.*a* and 1.*b*) being located above the cloth beam (5), further comprising a first frame (9.*a*) and a second frame (9.*b*), the first frame (9.*a*) having one of the warp beams (1.*a*) and one of the guide beams (2.*a*), the second frame (9.*b*) having another one of the warp beams (1.*b*) and another one of the guide beams (2.*b*), wherein the first frame (9.*a*) is movable relative to the second frame (9.*b*).

14. A method for producing of woven fabric while using a weaving loom (8) for inserting continuous material, or loosely connected material or material in pieces, the weaving loom comprising warp beams (1.*a*, 1.*b*), a cloth beam (5), hooks (3.*a*, 3.*b*), and guide beams (2.*a*, 2.*b*), wherein warp threads (4.*a* and 4.*b*) run in a downward direction from the warp beams (1.*a* and 1.*b*) to the cloth beam (5) and herein are individually held by the hooks (3.*a* and 3.*b*) which are anchored in the guide beams (2.*a* and 2.*b*) between the warp beams (1.*a* and 1.*b*) and the cloth beam (5), the warp beams (1.*a* and 1.*b*) being located above the cloth beam (5), wherein at least one of the guide beams (2.*a*, 2.*b*) is moved to converge the guide beams (2*a*, 2*b*) to each other, and wherein the weaving loom with converged guide beams (2.*a*, 2.*b*) is in a crossed position having a shed (19) which is closed toward the top and the weaving loom with non-converged guide beams (2.*a*, 2.*b*) is in a V-position having a V-shed (18) which is open toward the top.

15. The method as claimed in claim 14, wherein in the crossed position of the weaving loom (8) a weft thread (7) is introduced into the shed (19), and in that in the V-position of the weaving loom (8) at least one material strand (6) is placed into the open V-shed (18).

16. A woven fabric (20) having warp threads (4.*a*, 4.*b*) and weft threads (7), at least partially produced on a weaving loom (8) for inserting continuous material, or loosely connected material or material in pieces, the weaving loom comprising warp beams (1.*a*, 1.*b*), a cloth beam (5), hooks (3.*a*, 3.*b*), and guide beams (2.*a*, 2.*b*), wherein warp threads (4.*a* and 4.*b*) run in a downward direction from the warp beams (1.*a* and 1.*b*) to the cloth beam (5) and herein are individually held by the hooks (3.*a* and 3.*b*) which are anchored in the guide beams (2.*a* and 2.*b*) between the warp beams (1.*a* and 1.*b*) and the cloth beam (5), the warp beams (1.*a* and 1.*b*) being located above the cloth beam (5), wherein material strands (6), or at least one continuous material strand (6), are/is provided parallel to the weft threads (7) and alternating with the latter, and wherein the material strand (6) is different from the weft thread (7).

17. The woven fabric (20) as claimed in claim 16, wherein:
an irrigation hose (6-2); or
combinations (6-1, 6-2) of a wool strand (6-1) and an irrigation hose (6-2), is/are provided as material strands (6) or as a material strand (6).

18. The weaving loom as claimed in claim 6, wherein the mutual spacing corresponds to at least a largest width of the V-shed (18).

19. The weaving loom as claimed in claim 12, wherein the hooks (3.*a*, 3.*b*) have an end-proximal hook curvature of at least 370 degrees.

20. The weaving loom as claimed in claim 12, wherein the hooks (3.*a*, 3.*b*) are configured so as to be open, closed, or closed but openable.

21. The weaving loom as claimed in claim 13, wherein only one of the frames (9.*a*, 9.*b*) is movable.

22. The method as claimed in claim 15, wherein the material strand (6) is different from the weft thread (7).

\* \* \* \* \*